(12) United States Patent
Weber et al.

(10) Patent No.: US 7,767,219 B2
(45) Date of Patent: Aug. 3, 2010

(54) LOCALIZED DRUG DELIVERY USING DRUG-LOADED NANOCAPSULES

(75) Inventors: Jan Weber, Maple Grove, MN (US); Samuel Robaina, Plymouth, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1539 days.

(21) Appl. No.: 10/768,388

(22) Filed: Jan. 30, 2004

(65) Prior Publication Data

US 2005/0129727 A1 Jun. 16, 2005

Related U.S. Application Data

(60) Provisional application No. 60/443,950, filed on Jan. 31, 2003.

(51) Int. Cl.
*A61F 2/82* (2006.01)
(52) U.S. Cl. .................. 424/423; 977/810; 977/906
(58) Field of Classification Search .................. None
See application file for complete search history.

(56) References Cited

U.S. PATENT DOCUMENTS

| | | | |
|---|---|---|---|
| 5,304,121 A | 4/1994 | Sahatjian | 604/53 |
| 5,620,708 A | 4/1997 | Amkraut et al. | 424/491 |
| 5,693,034 A | 12/1997 | Buscemi et al. | 604/265 |
| 5,700,459 A | 12/1997 | Krone et al. | 424/78.08 |
| 5,702,754 A | 12/1997 | Zhong | 427/2.12 |
| 5,733,925 A | 3/1998 | Kunz et al. | 514/449 |

(Continued)

FOREIGN PATENT DOCUMENTS

WO  WO 99/47252   9/1999

(Continued)

OTHER PUBLICATIONS

Igor L. Radtchenko et al., "Assembly of Alternated Multivalent Ion/Polyelectrolyte Layers on Colloidal Particles. Stability of the Multilayers and Encapsulation of Macromolecules into Polyelectrolyte Capsules," *Journal of Colloid and Interface Science*, vol. 230, 1999, pp. 272-280.

(Continued)

*Primary Examiner*—Carlos A Azpuru
(74) *Attorney, Agent, or Firm*—Mayer & Williams PC; David B. Bonham; Keum J. Park

(57) ABSTRACT

Nanocapsules are disclosed which comprise (a) a drug-containing core and (b) a polyelectrolyte multilayer encapsulating the drug-containing core. The nanocapsules include particles whose largest dimension typically ranges between 50 nm to 10000 nm. In some embodiments, the nanocapsules contain a single drug. In others, the nanocapsules contain multiple drugs, either within the same nanocapsules or within separate populations of nanocapsules. In some embodiments, the nanocapsules comprise surfaces that are functionalized, for example, with ligands that allow for attachment to bodily tissue. In some embodiments of the present invention, the nanocapsules are rendered magnetic or are rendered susceptible to magnetic fields. Also disclosed is a drug delivery method that comprises the steps of (a) providing nanocapsules such as those above; and (b) placing the nanocapsules at a desired location within the body of a subject using an implantable or insertable medical device.

26 Claims, 2 Drawing Sheets

U.S. PATENT DOCUMENTS

| | | | | |
|---|---|---|---|---|
| 5,855,565 | A | 1/1999 | Bar-Cohen et al. | 604/104 |
| 5,921,244 | A | 7/1999 | Chen et al. | 128/897 |
| 6,060,534 | A | 5/2000 | Ronan et al. | 523/113 |
| 6,096,018 | A | 8/2000 | Luzio et al. | 604/500 |
| 6,176,849 | B1 | 1/2001 | Yang et al. | 604/265 |
| 6,184,266 | B1 | 2/2001 | Ronan et al. | 523/113 |
| 6,261,630 | B1 | 7/2001 | Nazarova et al. | 427/2.12 |
| 6,316,522 | B1 | 11/2001 | Loomis et al. | 523/105 |
| 6,479,146 | B1 | 11/2002 | Caruso et al. | 428/403 |
| 6,699,501 | B1 | 3/2004 | Sukhobukov et al. | 424/463 |
| 6,833,192 | B1 | 12/2004 | Caruso et al. | 428/403 |
| 2001/0012522 | A1 | 8/2001 | Ottoboni et al. | 424/501 |
| 2002/0058336 | A1 | 5/2002 | Ashkar | 435/368 |
| 2002/0082685 | A1 | 6/2002 | Sirhan et al. | 623/1.42 |
| 2002/0094569 | A1 | 7/2002 | Yu et al. | 435/325 |
| 2002/0107330 | A1 | 8/2002 | Pinchuk et al. | 525/242 |
| 2002/0187197 | A1 | 12/2002 | Caruso et al. | 424/490 |
| 2003/0003272 | A1 | 1/2003 | Laguitton | 428/141 |
| 2003/0007969 | A1 | 1/2003 | Lobb et al. | 424/144.1 |
| 2003/0065355 | A1 | 4/2003 | Weber | 606/200 |
| 2003/0187320 | A1 | 10/2003 | Freyman | 600/13 |
| 2003/0219909 | A1 | 11/2003 | Lally et al. | 436/518 |

FOREIGN PATENT DOCUMENTS

| | | |
|---|---|---|
| WO | WO 99/47253 | 9/1999 |
| WO | WO 00/03797 | 2/2000 |
| WO | WO 00/77281 | 12/2000 |
| WO | WO 01/51196 A1 | 2/2001 |
| WO | WO 02/09864 A1 | 2/2002 |
| WO | WO 02/09865 A1 | 2/2002 |
| WO | WO 02/17888 A2 | 3/2002 |
| WO | WO 03/037400 | 5/2003 |
| WO | WO 2004/014540 A1 | 2/2004 |
| WO | WO 2004/030648 A1 | 4/2004 |
| WO | WO 2004/047977 A1 | 6/2004 |

OTHER PUBLICATIONS

Lars Dähne et al., "Fabrication of Micro Reaction Cages with Tailored Properties," *J. Am. Chem. Soc.*, vol. 123, 2001, pp. 5431-5436.

Edwin W.H. Jager et al., "Microfabricating Conjugated Polymer Actuators," *Science*, vol. 290, Nov. 24, 2000, pp. 1540-1545.

Sergio Moya et al., "Lipid Coating on Polyelectrolyte Surface Modified Colloidal Particles and Polyelectrolyte Capsules," *Macromolecules*, vol. 33, 2000, pp. 4538-4544.

C. Gao et al., "Elasticity of Hollow Polyelectrolyte Capsules Prepared by the Layer-by-Layer Technique," *European Physical Journal E*, vol. 5, 2001, pp. 21-27.

Frank Caruso et al., "Microencapsulation of Uncharged Low Molecular Weight Organic Materials by Polyelectrolyte Multilayer Self-Assembly," *Langmuir*, vol. 16, 2000, pp. 8932-8936.

Igor L. Radtchenko et al., "A Novel Method for Encapsulation of Poorly Water-Soluble Drugs: Precipitation in Polyelectrolyte Multilayer Shells," *International Journal of Pharmaceutics*, vol. 242, 2002, pp. 219-223.

Information from Micromuscle.com website.; date unknown, but before the filing date of the instant application.

Capsulation product literature. 2002.

Catalogue of Certificate Reference Materials 2000-2001. Chemmea Bohemia s.r.o. www.labo.cz/chemmea/katalog/pages/particle.htm.

Dimitry G. Shchukin et al., "Micron-Scale Hollow Polyelectrolyte Capsules with Nanosized Magnetic $Fe_3O_4$ Inside," *Materials Letters*, vol. 57, 2003, pp. 1743-1747.

Gleb Sukhorukov et al., "Controlled Precipitation of Dyes into Hollow Polyelectrolyte Capsules Based on Colloids and Biocolloids," *Advanced Materials*, vol. 12, No. 2 (2000), pp. 112-115.

S. Moya et al., "Microencapsulation of Organic Solvents in Polyelectrolyte Multilayer Micrometer-Sized Shells," *Journal of Colloid and Interface Science*, vol. 216 (1999), pp. 297-302.

Alexei A. Antipov et al., "Polyelectrolyte Multilayer Capsule Permeability Control," *Colloids and Surfaces A: Physiochemical and Engineering Aspects*, 2002, pp. 535-541.

Miniscule Magnetic Particles Could Fight Cancer with Fewer Side Effects. Georgia Institute of Technology Press Release, Nov. 29, 2000. http://www.gatech.edu/news-room/archives/news_releases/zhang.html.

Catherine C. Berry et al., "Potential Drug-Cell Delivery Routes Using Magnetic Nanoparticles," *European Cells and Materials*, vol. 6, supplement 2, 2003, p. 29.

Nam Dinh et al., Magnetic Drug Targeting, University of California, Santa Barbara.

Xingping Qiu et al., "Studies on the Drug Release Properties of Polysaccharide Multilayers Encapsulated Ibuprofen Microparticles," *Langmuir*, vol. 17, 2001, pp. 5375-5380.

S. Moya et al., "Polyelectrolyte Multilayer Capsules Templated on Biological Cells: Core Oxidation Influences Layer Chemistry," *Colloids and Surfaces: A: Physicochemical and Engineering Aspects 183-185*, 2001, pp. 27-40.

Igor L. Radtchenko et al., "Incorporation of Macromolecules into Polyelectrolyte Micro- and Nanocapsules Via Surface Controlled Precipitation on Colloidal Particles," *Colloids and Surfaces: A: Physicochemical and Engineering Aspects 202*, 2002, pp. 127-133.

Winky L.W. Hau et al., "Surface-Chemistry Technology for Microfluidics," *J. Micromech. Microeng.*, vol. 13, 2003, pp. 272-278.

Gi-Ra Yi et al., "Ordered Macroporous Particles by Colloidal Templating," *Chem. Mater.*, vol. 13, 2001, pp. 2613-2618.

Alexei A. Antipov et al., "Sustained Release Properties of Polyelectrolyte Multilayer Capsules," *J. Phys. Chem. B*, vol. 105, 2001, pp. 2281-2284.

LOCALIZED DRUG DELIVERY USING DRUG-LOADED NANOCAPSULES

STATEMENT OF RELATED APPLICATION

This application claims the benefit of priority to U.S. provisional patent application No. 60/443,950 filed Jan. 31, 2003, which incorporated herein by reference in its entirety.

FIELD OF THE INVENTION

The present invention relates to controlled release nanocapsules, to devices and systems for their delivery, and to localized therapy using the same.

BACKGROUND OF THE INVENTION

Various medical devices have been developed for the delivery of therapeutic agents to the body. However, many challenges remain in providing drugs at desired target sites for sustained lengths of time.

For example, the problem of vascular injury presents a significant challenge during balloon angioplasty and coronary stenting procedures. Unfortunately, a limited number of controlled, long term, localized drug delivery systems have been developed that can address the complications of vascular injury, for example, endothelial denudation and exposure of the highly thrombotic subendothelial layer. Although some medical devices such as drug-coated stents provide a vehicle for sustained localized delivery of therapeutic agents (e.g., immunosuppressive and/or antiproliferative agents), other medical devices such as balloon angioplasty devices do not.

The present invention addresses these and other needs in the field.

SUMMARY OF THE INVENTION

In accordance with various aspects of the invention, nanocapsules are provided which comprise (a) a drug-containing core and (b) a polyelectrolyte multilayer encapsulating the drug-containing core. As their name suggests, the nanocapsules include particles whose largest dimension is nanometer in scale, typically 50 nm to 10000 nm in largest dimension. In some embodiments, the nanocapsules contain a single drug. In others, the nanocapsules contain multiple drugs, either within the same nanocapsules or within separate populations of nanocapsules.

Anti-restenosis drugs, such as paclitaxel, heparin, sirolimus, everolimus, tacrolimus, dexamethasone, estradiol, ABT-578 (Abbott Laboratories), trapidil, liprostin, Actinomcin D, Resten-NG, Ap-17, abciximab, clopidogrel and Ridogrel, are one exemplary group of drugs.

In some embodiments of the present invention, the nanocapsules comprise surfaces that are functionalized, for example, with ligands that allow for attachment to bodily tissue, for example, tissue associated with body lumens such as blood vessels, the gastrointestinal tract, the renal system, biliary system or pulmonary system. Integrins are one preferred group of ligands for functionalizing the surface of the nanocapsules, particularly those integrins that bind to laminin and/or collagen.

In some embodiments of the present invention, the nanocapsules are rendered magnetic or are rendered susceptible to magnetic fields (e.g., by incorporating a magnetic or paramagnetic material into the nanocapsules).

According to another aspect of the present invention, a drug delivery method is provided that comprises the steps of (a) providing nanocapsules such as those above; and (b) placing the nanocapsules at a desired location within the body of a subject using an implantable or insertable medical device.

In some embodiments, the desired location is the wall of a body lumen, for instance, a site of vascular injury.

In some embodiments, implantable or insertable medical devices are provided, which comprise ligand-functionalized nanocapsules, such as those described above. The nanocapsules are then delivered by inserting or planting such a device within a patient. For example, the nanocapsules can be provided within a biodegradable coating layer that is disposed over at least a portion of the surface of the medical device, whereupon the nanocapsules are released upon degradation of the biodegradable coating layer. As another example, the nanocapsules can be released by injecting a fluid that comprises the nanocapsules from the medical device into the patient.

In some embodiments, the medical device is an expandable medical device, such as an expandable stent or a balloon catheter, which has nanocapsules releasably disposed at an outer surface. As a specific example, functionalized nanocapsules such as those discussed above can be provided within a hydrogel layer. If desired, the medical device can further be provided with a retractable sheath to prevent premature release of the nanocapsules. Once the desired site of injury is reached, the sheath (if any) is pulled back, and the device is expanded, allowing the nanocapsules to emerge and attach to adjacent tissue.

In some embodiments, the medical device is adapted to provide an isolated region or "compartment," which is bounded by (a) the device and (b) bodily tissue (e.g., the wall of a body lumen). Once this compartment is established, nanocapsules with functionalized surfaces such as those described above, can be released into the same. After allowing a sufficient time for attachment, unattached particles can be removed from the compartment prior to device removal (e.g., by vacuum), if desired, thereby limiting the systemic effects of the drug.

In some embodiments, the nanocapsules are magnetic (e.g., they contain magnetized materials) or are at least susceptible to magnetic fields (e.g., they contain paramagnetic materials such as iron). At the same time, the implantable or insertable device is adapted to attract such nanocapsules, for example, (i) by having an associated magnetic field (e.g., because it contains permanent magnets or electromagnets), in which case both magnetized and paramagnetic nanocapsules will be attracted or (ii) by containing one or more paramagnetic materials (e.g., iron), in which case magnetized particles will be attracted to the device.

In some of these embodiments, the implantable or insertable medical device is first positioned within a subject, after which the nanocapsules are introduced into the vicinity of the device (e.g., by injection, ingestion, etc.), whereupon the nanocapsules become attached to the medical device. Subsequent to nanocapsule attachment, encapsulated drug(s) is(are) released in a controlled fashion at the site of the device. In addition, this embodiment of the invention allows for the replenishment of drug at the site of the device.

In some of these embodiments, the nanocapsules are magnetically attached to the medical device prior to insertion or implantation into the patient. If desired, the nanocapsules can be released subsequent to implantation or insertion of the device, for example, by gradual or immediate reduction in a magnetic field that is associated with the device.

In accordance with other aspect of the invention, the implantable or insertable medical device is an electroactive-polymer-actuated (EAP-actuated) device. In some embodiments, the EAP-actuated device will comprise an electroactive polymer layer and an adjacent conductive layer. One typical device is an EAP-actuated stent, which shrinks upon application of an appropriate electrical potential and expands to contact a body lumen upon the removal of that potential. In some instances, nanocapsules such as those discussed above are releasably disposed at an outer surface of the EAP-actuated device, in which case the device can be removed after particle attachment. In other instances, nanocapsules are attached to the outer surface of the device, in which case the device can be removed after a significant amount of drug release has occurred. In still other instances, the device is provided with a radioactive surface, for example, by providing encapsulated radioactive isotopes, to provide radiotherapy to an adjacent tissue.

These and other aspects, embodiments and advantages of the present invention will become immediately apparent to those of ordinary skill in the art upon reading the disclosure to follow.

DETAILED DESCRIPTION OF THE INVENTION

Figure 1:
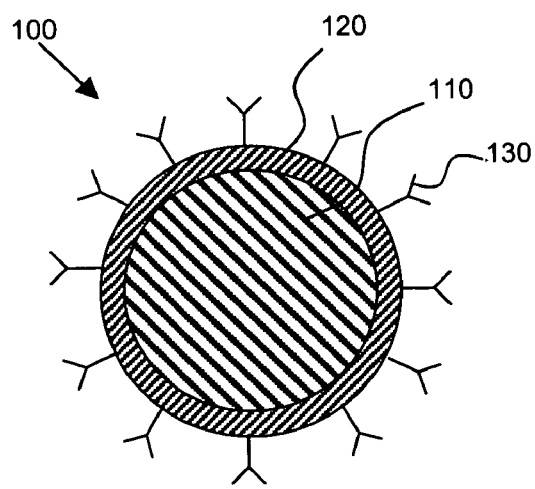
FIG. 1 is a schematic illustration of a nanocapsule with a functionalized surface, in accordance with an embodiment of the invention.

The present invention is directed to, inter alia, controlled drug delivery nanocapsules, to devices and systems for their delivery, and to localized therapy using the same.

According one aspect of the present invention, nanocapsules are provided, which comprise (a) a drug-containing core and (b) a polyelectrolyte multilayer encapsulating the drug-containing core.

Such nanocapsules can be prepared, for example, using various known layer-by-layer (LbL) techniques. LbL techniques typically entail coating particles, which are dispersed in aqueous media, via nanoscale, electrostatic, self-assembly using charged polymeric (polyelectrolyte) materials. These techniques exploit the fact that the particles serving as templates for the polyelectrolyte layers each has a surface charge, which renders them water dispersible and provides the charge necessary for adsorption of subsequent layers (i.e., polyelectrolyte multilayer encapsulation). The charge on the outer layer is reversed upon deposition of each sequential polyelectrolyte layer. Such multilayer shells are known to provide controlled drug release. For example, shell properties such as thickness and permeability can be tuned to provide an appropriate release profile.

Numerous materials, such as proteins, have an inherent surface charge that is present on particles made from the same. Examples of charged polymeric therapeutic agents include polynucleotides (e.g., DNA and RNA) and polypeptides (e.g., proteins, whose overall net charge will vary with pH, based on their respective isoelectric points), among others. For example, insulin is a negatively charged molecule at neutral pH, while protamine is positively charged.

Other materials, for example, many solid and liquid organic compounds, are uncharged. Such materials, however, can nonetheless be encapsulated by LbL technique by (a) providing the compound in finely divided form using, for instance, (i) colloid milling or jet milling or precipitation techniques, to provide solid particles, or (ii) emulsion technique to provide liquid particles within a continuous liquid or gel phase. The particles are provided with a surface charge, for example, by providing least one amphiphilic substance (e.g., an ionic surfactant, an amphiphilic polyelectrolyte or polyelectrolyte complex, or a charged copolymer of hydrophilic monomers and hydrophobic monomers) at the phase boundary between the solid/liquid template particles and the continuous phase (typically an aqueous phase).

Once a charged template particle is provided, it can be coated with a layer of an oppositely charged polyelectrolyte. Multilayers are formed by repeated treatment with oppositely charged polyelectrolytes, i.e., by alternate treatment with cationic and anionic polyelectrolytes. The polymer layers self-assemble onto the pre-charged solid/liquid particles by means of electrostatic, layer-by-layer deposition, thus forming a multilayered polymeric shell around the cores.

Amphiphilic substances include any substance, which has hydrophilic and hydrophobic groups. The amphiphilic substance should have at least one electrically charged group to provide the template particle (solid or liquid) with an electrical charge. Therefore, the amphiphilic substances used also can be referred to as ionic amphiphilic substances. Amphiphilic polyelectrolytes can be used as amphiphilic substances, for example, polyelectrolytes comprising charged groups as hydrophilic group and hydrophobic groups, e.g. aromatic groups, such as poly(styrene sulfonate) (PSS). Cationic and anionic surfactants can also be used as amphiphilic substances. Cationic surfactants include quaternary ammonium salts ($R_4N^+X^-$), for example, didodecyldimethylammonium bromide (DDDAB), alkyltrimethylammonium bromides such as hexadecyltrimethylammonium bromide (HDTAB), dodecyltrimethylammonium bromide (DTMAB), myristyltrimethylammonium bromide (MTMAB), or palmityl trimethylammonium bromide, or N-alkylpyridinium salts, or tertiary amines ($R_3NH^+X^-$), for example, cholesteryl-3β-N-(dimethyl-aminoethyl)-carbamate or mixtures thereof, wherein $X^-$ is a counteranion, e.g. a halogenide. Anionic surfactants include alkyl or olefin sulfate ($R-OSO_3M$), for example, a dodecyl sulfate such as sodium dodecyl sulfate (SDS), a lauryl sulfate such as sodium lauryl sulfate (SLS), or an alkyl or olefin sulfonate ($R-SO_3M$), for example, sodium-n-dodecyl-benzene sulfonate, or fatty acids ($R-COOM$), for example, dodecanoic acid sodium salt, or phosphoric acids or cholic acids or fluoro-organics, for example, lithium-3-[2-(perfluoroalkyl)ethylthio]propionate or mixtures thereof, where R is an organic radical and M is a countercation.

Polyelectrolytes are polymers having ionically dissociable groups, which can be a component or substituent of the polymer chain. Usually, the number of these ionically dissociable groups in the polyelectrolytes is so large that the polymers in dissociated form (also called polyions) are water-soluble. Depending on the type of dissociable groups, polyelectrolytes are typically classified as polyacids and polybases. When dissociated, polyacids form polyanions, with protons being split off, which can be inorganic, organic and biopolymers. Examples of polyacids are polyphosphoric acids, polyvinylsulfuric acids, polyvinylsulfonic acids, polyvinylphosphonic acids and polyacrylic acids. Examples of the corresponding salts, which are also called polysalts, are polyphosphates, polyvinylsulfates, polyvinylsulfonates, polyvinylphosphonates and polyacrylates. Polybases contain groups which are capable of accepting protons, e.g., by reaction with acids, with a salt being formed. Examples of polybases having dissociable groups within their backbone and/or side groups are polyallylamine, polyethylimine, polyvinylamine and polyvinylpyridine. By accepting protons, polybases form polycations.

Suitable polyelectrolytes according to the invention include those based on biopolymers such as alginic acid, gummi arabicum, nucleic acids, pectins and proteins, chemically modified biopolymers such as carboxymethyl cellulose and lignin sulfonates, and synthetic polymers such as polymethacrylic acid, polyvinylsulfonic acid, polyvinylphosphonic acid and polyethylenimine. Linear or branched polyelectrolytes can be used. Using branched polyelectrolytes can lead to less compact polyelectrolyte multilayers having a higher degree of wall porosity. Polyelectrolyte molecules can be crosslinked within or/and between the individual layers, e.g. by crosslinking amino groups with aldehydes, for example, to increase capsule stability. Furthermore, amphiphilic polyelectrolytes, e.g. amphiphilic block or random copolymers having partial polyelectrolyte character, can be used to reduce permeability towards polar small molecules. Such amphiphilic copolymers consist of units having different functionality, e.g. acidic or basic units, on the one hand, and hydrophobic units, on the other hand, such as styrenes, dienes or siloxanes which can be present in the polymer as blocks or distributed statistically.

By using polyelectrolytes that are degradable the release of enclosed drug can be further controlled via the dissolution of the capsule walls. Examples include polyglycolic acid (PGA), polylactic acid (PLA), polyamides, poly-2-hydroxybutyrate (PHB), polycaprolactone (PCL) and poly(lactic-coglycolic)acid (PLGA), protamine sulfate, polyallylamine, polydiallyldimethylammoniume, polyethyleneimine, chitosan, eudragit, gelatin, spermidine, albumin, polyacrylic acid, sodium alginate, polystyrene sulfonate, hyaluronic acid, carrageenin, chondroitin sulfate, carboxymethylcellulose, heparin, other polypeptides and proteins, and DNA, among others.

Basically, there are no limitations with regard to the polyelectrolytes to be used, as long as the molecules used have sufficiently high charge or/and are capable of binding with the layer beneath via other kinds of interaction, e.g., hydrogen bonds and/or hydrophobic interactions. Suitable polyelectrolytes, thus, include low-molecular weight polyelectrolytes, e.g., having molecular weights of a few hundred Daltons, up to macromolecular polyelectrolytes, e.g. polyelectrolytes of biological origin, having a molecular weight of several million Daltons.

Specific examples of polycations include protamine sulfate polycations, poly(allylamine) polycations (e.g., poly(allylamine hydrochloride) (PAH)), polydiallyldimethylammonium polycations, polyethyleneimine polycations, chitosan polycations, eudragit polycations, gelatine polycations, spermidine polycations and albumin polycations. Specific examples of polyanions include, and poly(styrenesulfonate) polyanions (e.g., poly(sodium styrenesulfonate) (PSS)), polyacrylic acid polyanions, sodium alginate polyanions, eudragit polyanions, gelatin polyanions, hyaluronic acid polyanions, carrageenan polyanions, chondroitin sulfate polyanions, and carboxymethylcellulose polyanions.

Other techniques take advantage of gradients across the capsule wall to effect precipitation or synthesis of a desired substance within the shell. For example, large macromolecules such as polymers cannot penetrate polyelectrolyte multilayers, while small solutes, for example, small molecule pharmaceuticals, can. Accordingly, the presence of macromolecules inside the capsules will lead to a difference in the physico-chemical properties between the bulk and the capsule interior, providing, for example, gradients in pH and/or polarity, which can be used to precipitate/synthesize materials within the capsules. Typically, a macromolecule is provided on the interior of the capsule by forming a double shell polyelectrolyte structure, after which the inner shell is decomposed.

For example, nanocapsules have been made by means of layer-by-layer adsorption of oppositely charged polyelectrolytes (i.e., an outer shell of alternating PAH and PSS) on an yttrium$^{3+}$/PSS inner shell, which is further disposed on the surface of colloidal template particles (i.e., melamine formaldehyde particles). Subsequently, the melamine formaldehyde core is removed, followed by the decomposition of the Yttrium$^{3+}$/PSS inner shell. A solution of a poorly water-soluble drug in an organic solvent (e.g., acetone) is then mixed with a water suspension of the capsules and diluted with acetone until complete dissolution of the drug is achieved. The organic solvent is then allowed to evaporate. The presence of the free polyelectrolyte molecules in the core results in a higher water concentration within the core, relative to the bulk. Because the concentration of water is higher in the core than in the bulk, the drug precipitates within the core, producing a drug-loaded nanocapsule. Additional information can be found, for example, in "A Novel Method for Encapsulation of Poorly Water-soluble Drugs: Precipitation in Polyelectrolyte Multilayer Shells," I. L. Radtchenko et al., *International Journal of Pharmaceutics*, 242, 219-223 (2002), the disclosures of which is hereby incorporated by reference.

As another example, the selective inorganic synthesis of magnetite ($Fe_3O_4$) inside poly(styrene sulfonate)/poly(allylamine hydrochloride) polyelectrolyte capsules of micron scale as been carried out. Micron and submicron sized capsules are made by means of layer-by-layer adsorption of oppositely charged polyelectrolytes (PSS, PAH) on the surface of colloidal template particles (e.g., weakly cross-linked melamine formaldehyde particles having a precipitated PAH-citrate complex) with subsequent degradation of the template core. This leaves free PAH in the core, which creates a pH gradient across the shell. At this point, (a) negatively charged, preformed magnetic particles of sufficiently small size (e.g., $Fe_3O_4$ nanoparticles) can be used to impregnate the capsules whereupon they are held by electrostatic interactions, or (b) magnetic material (e.g., $Fe_3O_4$) is selectively synthesized inside the core based on the pH gradient and on the presence of dissolved PAH in the capsule. The resulting capsules are easily driven by a magnetic field. Additional information can be found, for example, in "Micron-Scale Hollow Polyelectrolyte Capsules with Nanosized Magnetic $Fe_3O_4$ Inside, "*Materials Letters*, D. G. Shchukin et al. (in press), the disclosure of which is hereby incorporated by reference.

Yet more information on the formation of nanocapsules can be found, for example, in U.S. Patent Application 20020187197, WO 99/47252, WO 00/03797, WO 00/77281, WO 01/51196, WO 02/09864, WO 02/09865, WO 02/17888, "Fabrication of Micro Reaction Cages with Tailored Properties," L. Dähne et al., *J. Am. Chem. Soc.*, 123, 5431-5436 (2001), "Lipid Coating on Polyelectrolyte Surface Modified Colloidal Particles and Polyelectrolyte Capsules," Moya et al., *Macromolecules*, 33, 4538-4544 (2000), "Microencapsulation of Organic Solvents in Polyelectrolyte Multilayer Micrometer-sized Shells," S. Moya et al., *Journal of Colloid and Interface Science*, 216, 297-302 (1999); "Assembly of Alternated Multivalent Ion/Polyelectrolyte Layers on Colloidal Particles," I. L. Radtchenko et al., *Journal of Colloid and Interface Science*, 230, 272-280 (2000); "Controlled Precipitation of Dyes into Hollow Polyelectrolyte Capsules," G. Sukhorukov et al., *Advanced Materials*, Vol. 12, No. 2, 112-115 (2000), the disclosures of which are hereby incorporated by reference.

The wall thickness provided by the above layer-by-layer techniques will frequently range, for example, from 4 to 1000 nm. For example, a typical PAH/PSS single layer thickness is 1.5 nm. For proteins, however, much larger thicknesses are frequently encountered. The size of the resulting nanocapsules will frequently range, for example, from 50 to 10,000 nm.

Using techniques such as those discussed above, a single drug can be encapsulated within a single nanocapsule. Moreover, two or more populations of such nanocapsules, each containing a different drug, can be combined to provide for the release of multiple drugs. In addition, two or more drugs can be encapsulated within a single nanocapsule, for example in the core, or within multiple drug regions. For instance, a first drug (e.g., a drug that addresses smooth muscle cell proliferation or inflammatory responses) can be provided in an inner region such as the core, an inner multilayer encapsulation can surround the core (e.g., to address drug interaction and/or delay diffusion), an additional layer containing a second drug (e.g., a drug that addresses acute arterial injury) can then be provided over the inner multilayer encapsulation, and an outer multilayer encapsulation can be provided over the layer containing the second drug.

"Drugs," "therapeutic agents," "pharmaceutically active agents," "pharmaceutically active materials," and other related terms may be used interchangeably herein and include genetic therapeutic agents, non-genetic therapeutic agents and cells. Therapeutic agents may be used singly or in combination.

Exemplary non-genetic therapeutic agents for use in connection with the present invention include: (a) anti-thrombotic agents such as heparin, heparin derivatives, urokinase, and PPack (dextrophenylalanine proline arginine chloromethylketone); (b) anti-inflammatory agents such as dexamethasone, prednisolone, corticosterone, budesonide, estrogen, sulfasalazine and mesalamine; (c) antineoplastic/antiproliferative/anti-miotic agents such as paclitaxel, 5-fluorouracil, cisplatin, vinblastine, vincristine, epothilones, endostatin, angiostatin, angiopeptin, monoclonal antibodies capable of blocking smooth muscle cell proliferation, and thymidine kinase inhibitors; (d) anesthetic agents such as lidocaine, bupivacaine and ropivacaine; (e) anti-coagulants such as D-Phe-Pro-Arg chloromethyl ketone, an RGD peptide-containing compound, heparin, hirudin, antithrombin compounds, platelet receptor antagonists, anti-thrombin antibodies, anti-platelet receptor antibodies, aspirin, prostaglandin inhibitors, platelet inhibitors and tick antiplatelet peptides; (f) vascular cell growth promoters such as growth factors, transcriptional activators, and translational promotors; (g) vascular cell growth inhibitors such as growth factor inhibitors, growth factor receptor antagonists, transcriptional repressors, translational repressors, replication inhibitors, inhibitory antibodies, antibodies directed against growth factors, antibodies recognizing receptors on endothelial progenitor cells, proteins of the tetraspanin family, such as CD9 Beta-1 and Beta-3 integrins, CD63, CD81, FcgammaRII, bifunctional molecules consisting of a growth factor and a cytotoxin, bifunctional molecules consisting of an antibody and a cytotoxin; (h) protein kinase and tyrosine kinase inhibitors (e.g., tyrphostins, genistein, quinoxalines); (i) prostacyclin analogs; (j) cholesterol-lowering agents; (k) angiopoietins; (l) antimicrobial agents such as triclosan, cephalosporins, aminoglycosides and nitrofurantoin; (m) cytotoxic agents, cytostatic agents and cell proliferation affectors; (n) vasodilating agents; (o) agents that interfere with endogenous vasoactive mechanisms; (p) inhibitors of leukocyte recruitment, such as monoclonal antibodies; (q) cytokines; and (r) hormones. Preferred non-genetic therapeutic agents include paclitaxel, sirolimus, everolimus, tacrolimus, dexamethasone, halofuginone, cladribine, estradiol, ABT-578 (Abbott Laboratories), trapidil, liprostin, Actinomcin D, Resten-NG, Ap-17, abciximab, clopidogrel and Ridogrel.

Exemplary genetic therapeutic agents for use in connection with the present invention include anti-sense DNA and RNA as well as DNA coding for: (a) anti-sense RNA, (b) tRNA or rRNA to replace defective or deficient endogenous molecules, (c) angiogenic and other factors including growth factors such as acidic and basic fibroblast growth factors, vascular endothelial growth factor, endothelial mitogenic growth factors, epidermal growth factor, transforming growth factor α and β, platelet-derived endothelial growth factor, platelet-derived growth factor, tumor necrosis factor α, hepatocyte growth factor and insulin-like growth factor, (d) cell cycle inhibitors including CD inhibitors, and (e) thymidine kinase ("TK") and other agents useful for interfering with cell proliferation. Also of interest is DNA encoding for the family of bone morphogenic proteins ("BMP's"), including BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15, and BMP-16. Currently preferred BMP's are any of BMP-2, BMP-3, BMP-4, BMP-5, BMP-6 and BMP-7. These dimeric proteins can be provided as homodimers, heterodimers, or combinations thereof, alone or together with other molecules. Alternatively, or in addition, molecules capable of inducing an upstream or downstream effect of a BMP can be provided. Such molecules include any of the "hedgehog" proteins, or the DNA's encoding them.

Vectors for delivery of genetic therapeutic agents include viral vectors such as adenoviruses, gutted adenoviruses, adeno-associated virus, retroviruses, alpha virus (Semliki Forest, Sindbis, etc.), lentiviruses, herpes simplex virus, replication competent viruses (e.g., ONYX-015) and hybrid vectors; and non-viral vectors such as artificial chromosomes and mini-chromosomes, plasmid DNA vectors (e.g., pCOR), cationic polymers (e.g., polyethyleneimine, polyethyleneimine (PEI)), graft copolymers (e.g., polyether-PEI and polyethylene oxide-PEI), neutral polymers PVP, SP1017 (SUPRATEK), lipids such as cationic lipids, liposomes, lipoplexes, nanoparticles, or microparticles, with and without targeting sequences such as the protein transduction domain (PTD).

Cells for use in connection with the present invention include cells of human origin (autologous or allogeneic), including whole bone marrow, bone marrow derived mononuclear cells, progenitor cells (e.g., endothelial progenitor cells), stem cells (e.g., mesenchymal, hematopoietic, neuronal), pluripotent stem cells, fibroblasts, myoblasts, satellite cells, pericytes, cardiomyocytes, skeletal myocytes or macrophage, or from an animal, bacterial or fungal source (xenogeneic), which can be genetically engineered, if desired, to deliver proteins of interest.

Numerous therapeutic agents, not exclusive of those listed above, have been identified as candidates for vascular treatment regimens, for example, as agents targeting restenosis. Such agents are useful for the practice of the present invention and include one or more of the following: (a) Ca-channel blockers including benzothiazapines such as diltiazem and clentiazem, dihydropyridines such as nifedipine, amlodipine and nicardapine, and phenylalkylamines such as verapamil, (b) serotonin pathway modulators including: 5-HT antagonists such as ketanserin and naftidrofuryl, as well as 5-HT uptake inhibitors such as fluoxetine, (c) cyclic nucleotide pathway agents including phosphodiesterase inhibitors such as cilostazole and dipyridamole, adenylate/Guanylate cyclase stimulants such as forskolin, as well as adenosine analogs, (d) catecholamine modulators including α-antagonists such as prazosin and bunazosine, β-antagonists such as propranolol and α/β-antagonists such as labetalol and carvedilol, (e) endothelin receptor antagonists, (f) nitric oxide donors/releasing molecules including organic nitrates/nitrites such as nitroglycerin, isosorbide dinitrate and amyl nitrite, inorganic nitroso compounds such as sodium nitroprusside, sydnonimines such as molsidomine and linsidomine, nonoates such as diazenium diolates and NO adducts of alkanediamines, S-nitroso compounds including low molecular weight compounds (e.g., S-nitroso derivatives of captopril, glutathione and N-acetyl penicillamine) and high molecular weight compounds (e.g., S-nitroso derivatives of proteins, peptides, oligosaccharides, polysaccharides, synthetic polymers/oligomers and natural polymers/oligomers), as well as C-nitroso-compounds, O-nitroso-compounds, N-nitroso-compounds and L-arginine, (g) ACE inhibitors such as cilazapril, fosinopril and enalapril, (h) ATII-receptor antagonists such as saralasin and losartan, (i) platelet adhesion inhibitors such as albumin and polyethylene oxide, (j) platelet aggregation inhibitors including aspirin and thienopyridine (ticlopidine, clopidogrel) and GP IIb/IIIa inhibitors such as abciximab, epitifibatide and tirofiban, (k) coagulation pathway modulators including heparinoids such as heparin, low molecular weight heparin, dextran sulfate and β-cyclodextrin tetradecasulfate, thrombin inhibitors such as hirudin, hirulog, PPACK (D-phe-L-propyl-L-arg-chloromethylketone) and argatroban, FXa inhibitors such as antistatin and TAP (tick anticoagulant peptide), Vitamin K inhibitors such as warfarin, as well as activated protein C, (l) cyclooxygenase pathway inhibitors such as aspirin, ibuprofen, flurbiprofen, indomethacin and sulfinpyrazone, (m) natural and synthetic corticosteroids such as dexamethasone, prednisolone, methprednisolone and hydrocortisone, (n) lipoxygenase pathway inhibitors such as nordihydroguairetic acid and caffeic acid, (o) leukotriene receptor antagonists, (p) antagonists of E- and P-selectins, (q) inhibitors of VCAM-1 and ICAM-1 interactions, (r) prostaglandins and analogs thereof including prostaglandins such as PGE1 and PGI2 and prostacyclin analogs such as ciprostene, epoprostenol, carbacyclin, iloprost and beraprost, (s) macrophage activation preventers including bisphosphonates, (t) HMG-CoA reductase inhibitors such as lovastatin, pravastatin, fluvastatin, simvastatin and cerivastatin, (u) fish oils and omega-3-fatty acids, (v) free-radical scavengers/antioxidants such as probucol, vitamins C and E, ebselen, trans-retinoic acid and SOD mimics, (w) agents affecting various growth factors including FGF pathway agents such as bFGF antibodies and chimeric fusion proteins, PDGF receptor antagonists such as trapidil, IGF pathway agents including somatostatin analogs such as angiopeptin and ocreotide, TGF-β pathway agents such as polyanionic agents (heparin, fucoidin), decorin, and TGF-β antibodies, EGF pathway agents such as EGF antibodies, receptor antagonists and chimeric fusion proteins, TNF-α pathway agents such as thalidomide and analogs thereof, Thromboxane A2 (TXA2) pathway modulators such as sulotroban, vapiprost, dazoxiben and ridogrel, as well as protein tyrosine kinase inhibitors such as tyrphostin, genistein and quinoxaline derivatives, (x) MMP pathway inhibitors such as marimastat, ilomastat and metastat, (y) cell motility inhibitors such as cytochalasin B, (z) antiproliferative/antineoplastic agents including antimetabolites such as purine analogs (6-mercaptopurine or cladribine, which is a chlorinated purine nucleoside analog), pyrimidine analogs (e.g., cytarabine and 5-fluorouracil) and methotrexate, nitrogen mustards, alkyl sulfonates, ethylenimines, antibiotics (e.g., daunorubicin, doxorubicin), nitrosoureas, cisplatin, agents affecting microtubule dynamics (e.g., vinblastine, vincristine, colchicine, paclitaxel and epothilone), caspase activators, proteasome inhibitors, angiogenesis inhibitors (e.g., endostatin, angiostatin and squalamine), rapamycin, cerivastatin, flavopiridol and suramin, (aa) matrix deposition/organization pathway inhibitors such as halofuginone or other quinazolinone derivatives and tranilast, (bb) endothelialization facilitators such as VEGF and RGD peptide, and (cc) blood rheology modulators such as pentoxifylline.

Numerous additional therapeutic agents useful for the practice of the present invention are also disclosed in U.S. Pat. No. 5,733,925 assigned to NeoRx Corporation, the entire disclosure of which is incorporated by reference.

A wide range of drug loading levels can be used in connection with the various embodiments of the present invention, with the amount of loading being readily determined by those of ordinary skill in the art and ultimately depending, for example, upon the condition to be treated, the nature of the therapeutic agent itself, the means by which the therapeutic agent is administered to the intended subject, and so forth.

In many embodiments of the present invention, the nanocapsules have a surface that is functionalized, for instance, with ligands that promote attachment to a targeted tissue. Examples of targeted tissue include tissue associated with the vascular system (e.g., the coronary and cerebral vasculature), the gastrointestinal system (e.g., the throat, esophagus, gut, intestines, colon), the urinary system (e.g., the urethra, bladder and ureters), the biliary system, and the pulmonary system (e.g., thorax and lungs).

For instance, ligands can be provided which bind to exposed subendothelium components, such as collagen. In general, in order for functionalized nanocapsules to attach to the subendothelium, the subendothelium is either exposed or the nanocapsules are introduced to the subendothelial layer. In some embodiments, it is desirable to prepare the surface, for example, by performing balloon angioplasty or PCTA, or by using a cutting balloon to expose the subendothelial layers.

Once attached, drug can diffuse from the nanocapsules into adjacent tissue at a predictable and controllable rate. A nanocapsule with a drug core 110, a biocompatible polyelectrolyte multilayer capsule 120, and a functionalized surface comprising a plurality of ligands 130 (one numbered), in accordance with an embodiment of the invention, is illustrated schematically in FIG. 1.

Integrins are a preferred class of ligands for functionalizing the surface of the nanocapsules of the present invention. Integrins recognize a wide variety of extracellular matrix components and cell-surface receptors, including collagen, fibronectin, vitronectin, laminin, fibrinogen, and adhesion molecules including intracellular adhesion molecules (ICAMS) and vascular adhesion molecules (VCAMS). Members of the integrin family of cell-surface receptors are expressed on virtually all mammalian cells and mediate adhesion of cells to one another and to the extracellular matrix.

Integrins are structurally and functionally related glycoproteins consisting of heterodimeric (alpha and beta) molecules. Preferred integrins are those which specifically bind to laminin and/or collagen, and can rapidly stabilize contact between the nanocapsules and, for example, the endothelium at a site of inflammation. Examples include several members of the integrin very late antigen (VLA) superfamily: (A) Alpha1/beta1 is a receptor for collagen-I, collagen-IV and laminin (E1 region). This integrin is also known as VLA-1 (very late activation antigen 1) and CD49a. (B) Alpha2/beta1 is a receptor for collagen-I to VI, laminin and possibly fibronectin. This receptor is also known as VLA-2 (very late activation antigen 2), GPIa-IIa(glycoprotein Ia-IIa on platelets) and ECMRII (extracellular matrix receptor II). (C) Alpha3/beta1 is a receptor for epiligrin, laminin (E3 fragment), nidogen/entactin, fibronectin and collagen-1. This integrin is also known as VLA-3 (very late activation antigen 3), VCA-2 (very common antigen 2), ECMRI (extracellular matrix receptor I) and Gapb-3 (galactoprotein b3). (D) Alpha6/beta1 is a receptor for laminin-1, laminin-2, laminin-4 and laminin-5. This receptor is also known as VLA-6 (very late activation antigen 6) and GPIc-IIa (glycoprotein Ic-IIa on platelets). (E) Alpha-6/beta-4 is a receptor for laminin-1 and laminin-5. Additional integrins are described, for example, in U.S. Pat. Appln. No. 20020058336 and U.S. Pat. Appln. No. 20030007969, the disclosures of which are hereby incorporated by reference.

Many techniques known in the art can be used to connect nanocapsules to ligands, including covalent attachment techniques, as well as non-covalent attachment techniques, such as ion exchange techniques, antibody-antigen techniques, nucleic hybridization techniques, and so forth. For instance, the polyelectrolyte making up the outer layer of the nanocapsule can be provided with reactive functional groups, or the surface of the nanocapsule can be treated with a reagent that places chemically reactive groups on the surface. These groups can then be used to directly or indirectly (e.g., using linking groups) bond the ligand of interest (e.g., an integrin) to the nanocapsule via reactive groups that are commonly found on the same, such as such as amines, alcohols, carboxylic acids, and thiols.

It should be noted that the present invention is not limited using a single type of ligand on the nanocapsule's surface. Nor is the surface functionalization limited to ligands. For example, one can mix nanocapsules that have distinct functionalized surface properties, or one can provide nanocapsules that have multiple surface ligands/receptors/etc. on their surfaces. Moreover, various surface actuators/triggers/receptors can be placed on the nanocapsule surface to enhance binding, migration into the tissue, and/or blocking platelet receptors.

In some embodiments of the present invention, nanocapsules are rendered magnetic or are rendered susceptible to magnetic fields. For example, a powder of a magnetized material or a paramagnetic material (typically metals, alloys or compounds of certain transition, rare earth and actinide elements, for example, iron) can be encapsulated within the nanocapsules, along with a drug. As a specific example, 0.9 micron ferrite magnet powders are available from Xiangying Magnetic Materials Co., Ltd., Xiamen 361009, China, which can provided with the nanocapsules.

Additional aspects of the present invention are directed to methods and systems for delivering the above nanocapsules. In many embodiments, the nanocapsules are delivered/placed at a desired location within a subject (e.g., a mammalian subject, preferably a human subject) using an implantable or insertable medical device.

The present invention is applicable to various medical devices that are implanted or inserted into the body, either for procedural uses or as implants. Implantable or insertable medical devices for use in conjunction with the present invention include catheters (for example, renal or vascular catheters such as balloon catheters), guide wires, balloons, filters (e.g., vena cava filters), stents (including coronary vascular stents, cerebral, urethral, ureteral, biliary, tracheal, gastrointestinal and esophageal stents), stent grafts, cerebral aneurysm filler coils (including Guglilmi detachable coils and metal coils), vascular grafts, venous valves, heart valves and biopsy devices.

In many embodiments, the medical device is adapted for placement and expansion in a bodily lumen, such as the lumens associated with the vascular, gastrointestinal, urinary, biliary and pulmonary systems. Examples of medical devices for placement and expansion in such bodily lumens include catheters (for example, renal or vascular balloon catheters), stents (for example, coronary vascular stents, cerebral, urethral, ureteral, biliary, tracheal, gastrointestinal and esophageal stents) and other implantable medical devices such as coils and embolic agents.

In some embodiments of the present invention, an expandable medical device is provided with a nanocapsule-containing layer on its surface. As a specific example, the medical device can be provided with an outer layer that comprises a hydrogel and the above nanocapsules.

Hydrogels are typically hydrophilic polymeric materials that have the ability to absorb large amounts of water or other polar molecules, up to many times the weight of the hydrogel itself. Hydrogels have been disclosed as coatings for implantable or insertable medical devices or as materials for constructing the device itself in, for example, U.S. Pat. Nos. 6,316,522; 6,261,630; 6,184,266; 6,176,849; 6,096,108; 6,060,534; 5,702,754; 5,693,034; and, 5,304,121, each of which is assigned to Boston Scientific Corporation or SciMed Life Systems, Inc. and is incorporated herein in its entirety by reference. Hydrogels, such as those described in the foregoing exemplary U.S. Patents, can be based on synthetic or naturally occurring materials, or a composite thereof; can be biodegradable or substantially non-biodegradable; and, can be modified or derivatized in numerous ways to render the hydrogel more suitable for a desired purpose. For example, the hydrogel can be modified by chemically cross-linking with, for example, a polyfunctional cross-linking agent that is reactive with functional groups covalently bonded to the polymer structure. The hydrogel polymer can also be ionically cross-linked with, for example, polyvalent metal ions. Many hydrogel polymers can be both chemically and ionically cross-linked. Examples of hydrogel polymers include polyacrylates; poly(acrylic acid); poly(methacrylic acid); polyhydroxyethyl methacrylates; polyacrylamides; poly(N-alkylacrylamides); polyalkylene oxides; poly(ethylene oxide); poly(propylene oxide); poly(vinyl alcohol); polyvinyl aromatics; poly(vinylpyrrolidone); poly(ethyleneimine); polyethylene amine; polyacrylonitrile; polyesters; polyvinyl sulfonic acid; polyamides; poly(L-lysine); hydrophilic polyurethanes; maleic anhydride polymers; proteins; fibrin; collagen; cellulosic polymers; methyl cellulose; carboxymethyl cellulose; dextran; carboxymethyl dextran; modified dextran; alginates; alginic acid; pectinic acid; hyaluronic acid; chitin; pullulan; elastin; laminin; agarose; gelatin; gellan; xanthan;

carboxymethyl starch; chondroitin sulfate; guar; starch; and copolymers, mixtures and derivatives thereof.

Figure 2A:
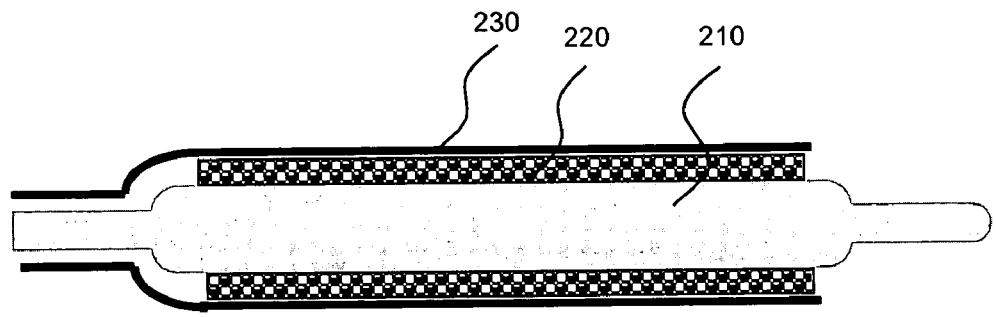
FIG. 2A is a schematic illustration, pre-inflation, of a balloon catheter drug delivery system, in accordance with an embodiment of the invention.
Figure 2B:
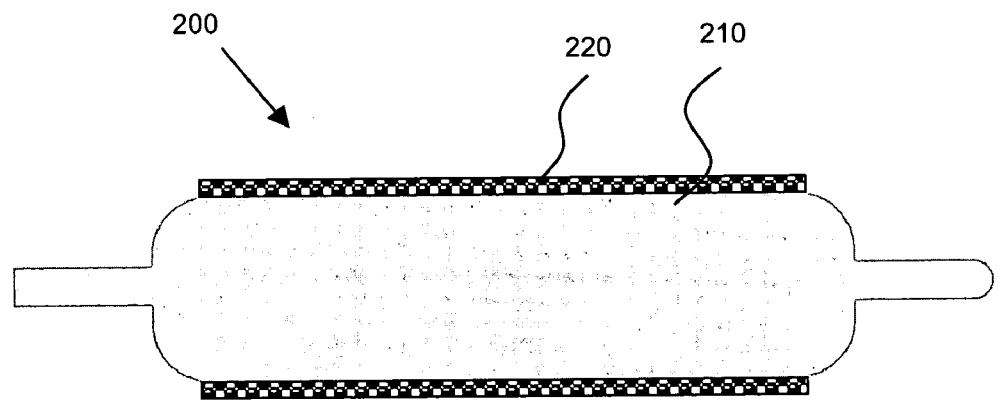
FIG. 2B is a schematic illustration of the balloon catheter drug delivery system of FIG. 2A post-inflation, in accordance with an embodiment of the invention.
Figure 3:
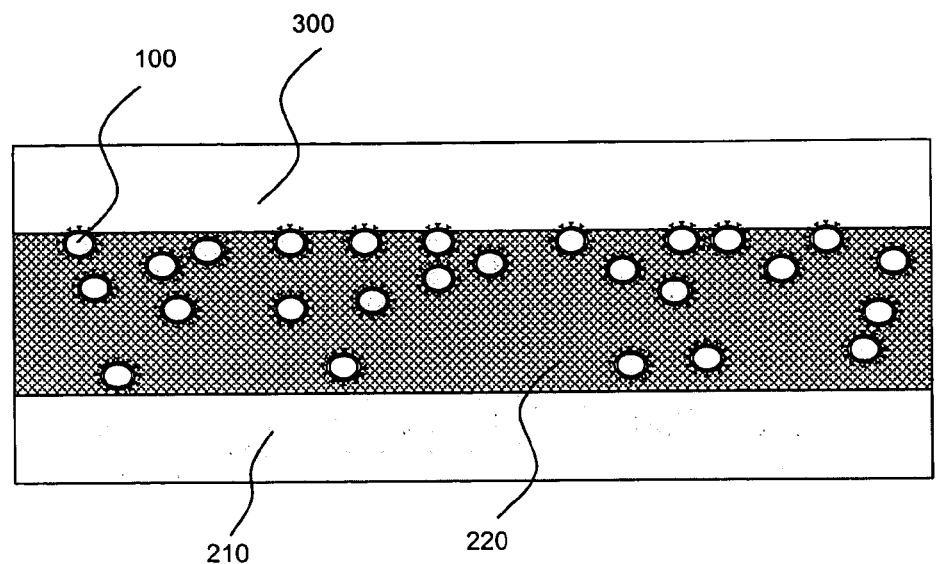
FIG. 3 a schematic diagram, which illustrates a portion of an outer layer of a balloon catheter having an outer nanocapsule-containing hydrogel layer that is disposed adjacent exposed subendothelium of a blood vessel, in accordance with an embodiment of the invention.

In one specific embodiment, a balloon catheter 200, which is illustrated schematically in FIG. 2A, is modified by addition of layer 220 comprising nanocapsules admixed with a hydrophobic (or hydrophilic) hydrogel, for example, to preserve the functionality of any attached ligands. The balloon catheter 200 is further modified by the addition of a sheath 230, which covers the nanocapsule/hydrogel layer in the embodiment illustrated. The balloon catheter 200 is adapted for insertion into a body lumen. Once the site of interest is reached, the sheath 230 is pulled back, exposing the nanocapsule-containing hydrogel layer 220, and the balloon is inflated as illustrated in FIG. 2B. A small schematic cross section illustrating a portion of the balloon 210, outer nanocapsule-containing hydrogel layer 220, and lumen tissue 300 (in this case, exposed subendothelium) is illustrated in FIG. 3. In this fashion, the nanocapsules 100 (one numbered) are delivered to the lumen wall 300, where they are allowed to attach via their functionalized surfaces. Subsequently, even though the balloon may be removed, the drug will continue to be released from the attached nanocapsules to the adjacent tissue in a controlled fashion.

In some embodiments of the invention, an electroactive polymer (EAP) actuated device is utilized as an expandable medical device. EAP-actuated devices are known. EAP-actuated devices for use in connection with the present invention can be quite simple, constructed of, for example, an electroactive polymer layer (e.g., a layer comprising polypyrrole, polyaniline, polysulfone or polyacetylene) adjacent a conductive layer, such as a metal foil (e.g., gold foil, silver foil, etc.), a conductive polymer layer (e.g., polymer layer having a conductive carbon coating), or carbon nanotube paper (sometimes referred to as "bucky paper").

A stent device of this type is manufactured by Micromuscle AB, Linköping, Sweden. When activated, the stent shrinks. When deactivated, the stent expands. Thus, once the device is placed inside a body lumen, for example, a blood vessel, electrical connection to an applied voltage is broken, and the device expands into contact with the vessel.

In one embodiment of the present invention, a nanocapsule-containing layer is applied to an EAP-actuated device like that described above. The nanocapsules can be applied to the surface of the EAP-actuated device in a variety of fashions including ionic bonding, hydrogen bonding, covalent bonding, physical entrapment, Van der Waals bonding, and bonding through hydrophilic/hydrophobic interactions. For example, the nanocapsules can be applied to the surface of the device via covalent attachment, or they can be entrapped in a polymeric layer such as the hydrogel layers discussed above. After reaching a site of intended release, the EAP is deactivated, and the device is deployed. After the nanocapsules have been given sufficient time to attach at the release site (for instance, in the event that the nanocapsules are releasable and functionalized for attachment) or after drug has been released for a sufficient time (for instance, in the event that the nanocapsules are not releasably attached to the device and/or are not functionalized for attachment), a voltage is reapplied to the device, whereupon the device contracts and is removed from the body.

In addition to chemotherapy using drugs, the above device can also be used to carry out radiotherapy, for example, by providing EAP-containing device with a radioactive surface (which can be provided, for example, by bonding radioactive powder or radioactive containing nanocapsules to the outside of the device).

In other embodiments of the invention, a medical device is implanted or inserted into the body whereupon the device is used to form an isolated region (or "compartment") adjacent the tissue to be treated. For instance, "dog bone" and "double sausage" balloon catheters are known in the art, which upon inflation, establish an isolated region, or compartment, whose boundaries are defined by the medical device and the body lumen. After such an isolated region is established using the medical device, nanocapsules functionalized for attachment to tissue, such as those as described above, are released into the isolated region (e.g., by injection within a buffered solution), allowing the nanocapsules to attach to the adjacent lumen wall (e.g., a blood vessel wall). After an allotted time period, excess injected material can be removed through the delivery device, for example, by suction or flushing action. This feature of the present invention is of value, for instance, where one wishes to reduce the spread of nanocapsules throughout the circulatory system.

Still other embodiments of the present invention utilize nanocapsules, such as those previously discussed, which are either magnetic (e.g., nanocapsules containing magnetic powder) or are susceptible to magnetic fields (e.g., nanocapsules containing a paramagnetic material, such as iron powder).

For example, in some embodiments, such nanocapsules are delivered to a desired location inside the body by first attaching them magnetically to a device (e.g., a catheter) while outside the body (e.g., by turning on a magnetic field, for instance, using a coil wound around a catheter). Subsequently, the device with attached capsules is guided to a desired location within the patient, whereupon and the magnetic field is turned off, thereby locally releasing the capsules. This manner of particle delivery is advantageous for a number of reasons. For example, in the case where the nanocapsules are released from a catheter to surrounding tissue, the delivery mechanism can be very simple (e.g., a coil) and only the nanocapsules need be provided on the outside of the device, thereby reducing the delivery profile of the device relative to various devices having alternate delivery mechanisms.

In other embodiments, a medical device is inserted into the subject, which is capable of attracting such particles, for instance, by virtue of it: (a) having a magnetic field (e.g., because it contains permanent magnets or electromagnets), in which case both magnetized and paramagnetic nanocapsules will be attracted or (b) containing one or more paramagnetic materials such as iron, in which case magnetized nanocapsules will be attracted.

After the medical device is properly positioned, the nanocapsules can be placed in the vicinity of the medical device (for example, by injection or ingestion), whereupon the nanocapsules become magnetically attached to the medical device. The nanocapsules subsequently release the encapsulated drug(s) in a controlled fashion at the site of the device. In this way, the medical device can be replenished periodically with drugs. In some embodiments, the device is provided with openings, for example, where the device is formed from wire or wires, or where the device is provided with apertures or windows, to ensure that the tissue adjacent the device is exposed to significant drug concentrations.

Figures 4A, 4B, 4C, 4D:
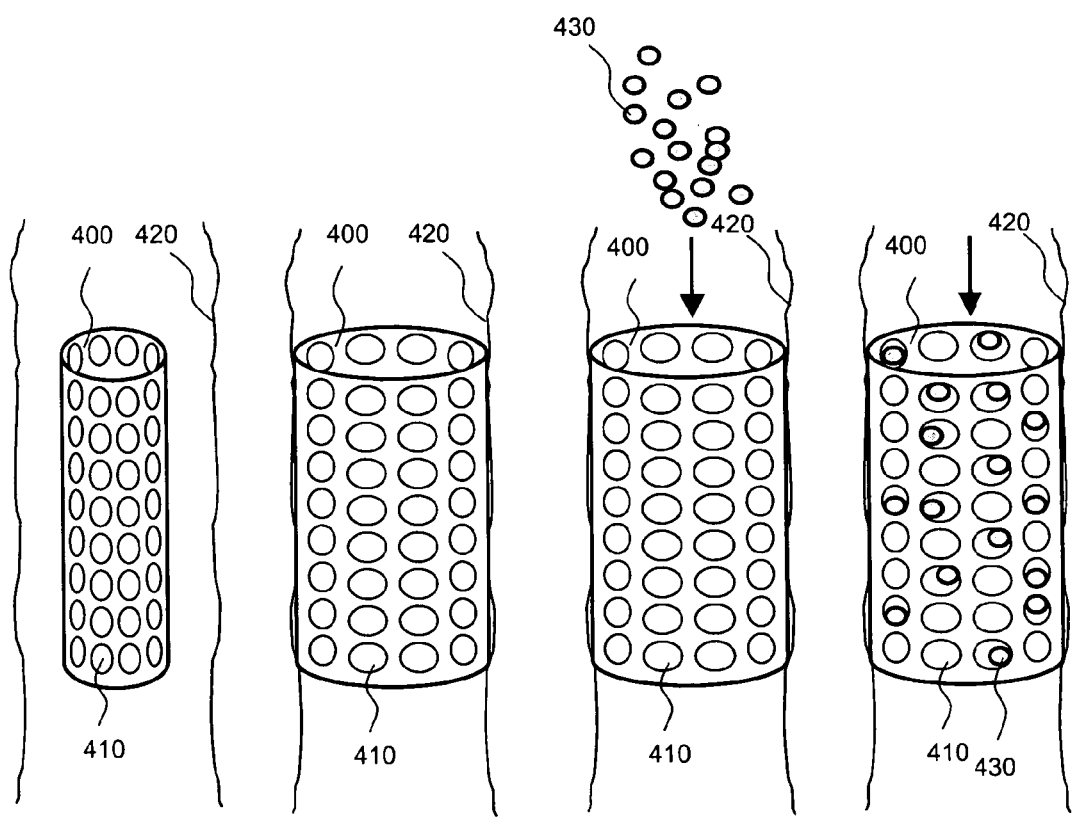
FIGS. 4A-4D are a series of schematic diagrams illustrating the insertion of an EAP-actuated medical device into the esophagus, followed by deployment of the device, and exposure to magnetic nanocapsules, in accordance with an embodiment of the invention.

A specific embodiment is illustrated schematically in FIGS. 4A-4D. FIG. 4A schematically illustrates the placement of an EAP-actuated stent 400 in a body lumen 420, in this case the esophagus. As noted above, the device can be quite simple, for example, a layer of metal foil that has been provided with a series of apertures 410 with an electroactive polymer layer attached on one side, which is able to expand and crimp the device inside the esophagus. The device can be rendered magnetic using a number of techniques. For example, the device can be equipped with magnets in the form of sheets, strips, wires or powders which can be sandwiched in EAP structure, attached to foil, woven into structure, and so forth. In this particular embodiment, a series of magnetic wires (not illustrated) are woven into the device 400. The depicted device 400 is held in a contracted state during delivery by the application of an appropriate electrical potential.

The applied electrical potential is then discontinued, allowing the device 400 to expand to meet the lumen walls 420 as illustrated in FIG. 4B. Once the device is expanded in the esophagus, the subject can periodically swallow a fluid containing magnetic beads 430 (one numbered) as schematically illustrated in FIG. 4C. At least some of the beads 430 are attracted to the device as they pass, replenishing the device 400. See FIG. 4D.

In some embodiments, medical devices are provided which comprise biodegradable coatings, within which are entrapped magnetic particles, such as magnetic nanoparticles. The magnetic particles, for example, can consist solely of a magnetic material (e.g., a ferromagnetic material) or they can contain an encapsulated magnetic material (e.g., a ferromagnetic material encapsulated within a polyelectrolyte multilayer shell). Like the nanocapsules of the present invention, the largest dimension of the magnetic nanoparticles is typically between 50 nm and 10000 nm.

Because the device is made magnetic in this embodiment by providing magnetic nanoparticles inside a biodegradable coating, upon implantation or insertion into a patient, the number of particles will diminish, making the device less magnetic over time. As a result, the ability of the device to attract and secure magnetic or paramagnetic materials, for example, magnetic or paramagnetic nanocapsules containing a drug, decreases. Similarly, the ability of a magnetic or paramagnetic apparatus to be secured to the medical device (e.g., securement systems for stents, gripping devices for vena cava filters, etc.) also diminishes over time. By providing such coatings, for example, one can utilize a core material for the medical device which is non-metallic or consists of a non-magnetic metal (e.g., niobium, titanium, etc.). This would allow, for example, one to visualize the medical device using MRI in a later stage, after the magnetic layer has been degraded and the device is without any appreciable magnetism.

Although various embodiments are specifically illustrated and described herein, it will be appreciated that modifications and variations of the present invention are covered by the above teachings without departing from the spirit and intended scope of the invention.

What is claimed is:

1. A medical device adapted for implantation or insertion into a patient, said medical device comprising a magnetic or paramagnetic region and a plurality of nanocapsules that are magnetically attracted to said magnetic or paramagnetic region, said nanocapsules comprising a therapeutic agent, a magnetic or paramagnetic material, and a polyelectrolyte multilayer shell.

2. The medical device of claim 1, wherein said medical device is a catheter or a guidewire.

3. The medical device of claim 1, wherein said medical device is an implant selected from a stent, a graft, a vena cava filter, a pacemaker, a heart valve and a venous valve.

4. The medical device of claim 1, wherein said medical device comprises a magnetic region.

5. The medical device of claim 4, wherein said magnetic region is a ferromagnetic region.

6. The medical device of claim 4, wherein said magnetic region is an electromagnetic region.

7. The medical device of claim 1, wherein said medical device comprises a plurality of distinct magnetic regions.

8. The medical device of claim 1, wherein the entirety of said medical device is magnetic or paramagnetic.

9. The medical device of claim 1, wherein said medical device comprises an electroactive polymer actuator.

10. The medical device of claim 1, wherein said nanocapsules comprise a magnetic material.

11. The medical device of claim 1, wherein said nanocapsules comprise a paramagnetic material.

12. The medical device of claim 1, wherein said medical device comprises a magnetic or paramagnetic region and said nanocapsules comprise a magnetic material.

13. An implantable or insertable medical device according to claim 1 wherein the nanocapsules further comprise a tissue specific ligand attached to an outer surface of said polyelectrolyte multilayer shell.

14. The medical device of claim 13, wherein said medical device is a catheter or a guidewire.

15. The medical device of claim 13, wherein said medical device is an implant selected from a stent, a graft, a vena cava filter, a pacemaker, a heart valve and a venous valve.

16. The medical device of claim 13, wherein said nanocapsules are provided within a coating layer that is disposed over at least a portion of the surface of said medical device.

17. The medical device of claim 16, wherein said coating layer is a hydrogel coating layer.

18. The medical device of claim 16, wherein said coating layer is a biodegradable coating layer.

19. The medical device of claim 18, wherein said biodegradable coating layer comprises a biodegradable polyelectrolyte.

20. The medical device of claim 19, wherein said polyelectrolyte is selected from gelatin and heparin.

21. The medical device of claim 13, wherein said medical device comprises a magnetic or paramagnetic region, wherein said nanocapsules comprise a magnetic or paramagnetic material, and wherein said nanocapsules are magnetically attracted to said magnetic or paramagnetic region of said medical device.

22. The medical device of claim 13, wherein said medical device comprises an electroactive polymer actuator.

23. The medical device of claim 4, wherein said magnetic region of said medical device comprises magnetic nanocapsules entrapped within a biodegradable coating.

24. The medical device of claim 9, wherein the device is a stent.

25. The medical device of claim 1 wherein the nanocapsules have a size in the range of 10-50 microns.

26. The medical device of claim 1 wherein the nanocapsules have a wall thickness in the range of 4-50 nm.

* * * * *